United States Patent
Hallundbæk et al.

(10) Patent No.: US 9,080,429 B2
(45) Date of Patent: Jul. 14, 2015

(54) SCANNING TOOL

(75) Inventors: Jørgen Hallundbæk, Græsted (DK); Ulrik Weiland Robenhagen, Lyngby (DK)

(73) Assignee: WELLTEC A/S, Allerød (DK)

( * ) Notice: Subject to any disclaimer, the term of this patent is extended or adjusted under 35 U.S.C. 154(b) by 274 days.

(21) Appl. No.: 13/505,211

(22) PCT Filed: Oct. 29, 2010

(86) PCT No.: PCT/EP2010/066462
§ 371 (c)(1),
(2), (4) Date: Apr. 30, 2012

(87) PCT Pub. No.: WO2011/051441
PCT Pub. Date: May 5, 2011

(65) Prior Publication Data
US 2012/0211649 A1    Aug. 23, 2012

(30) Foreign Application Priority Data
Oct. 30, 2009    (EP) ..................................... 09174666

(51) Int. Cl.
| G01V 5/08 | (2006.01) |
| E21B 47/10 | (2012.01) |
| E21B 47/00 | (2012.01) |
| G01N 21/954 | (2006.01) |

(52) U.S. Cl.
CPC ........... *E21B 47/102* (2013.01); *E21B 47/0002* (2013.01); *G01N 21/954* (2013.01)

(58) Field of Classification Search
CPC .. E21B 47/0002; E21B 47/102; G01N 21/954
USPC ....................................................... 250/269.1
See application file for complete search history.

(56) References Cited

U.S. PATENT DOCUMENTS

| 4,034,218 A | * | 7/1977 | Turcotte ..................... 250/269.3 |
| 4,042,823 A | * | 8/1977 | Decker et al. ............ 250/227.26 |
| 4,055,990 A | | 11/1977 | Topping |
| 4,255,798 A | * | 3/1981 | Havira ............................ 367/35 |
| 4,766,577 A | | 8/1988 | Clerke et al. |
| 4,855,820 A | | 8/1989 | Barbour |
| 4,992,656 A | * | 2/1991 | Clauser ......................... 250/251 |
| 5,012,091 A | * | 4/1991 | Moake .......................... 250/266 |

(Continued)

FOREIGN PATENT DOCUMENTS

| CN | 2384382 | 6/2000 |
| CN | 1846128 A | 10/2006 |

(Continued)

OTHER PUBLICATIONS

International Search Report for PCT/EP2010/066462, mailed Dec. 9, 2010.
International Preliminary Report on Patentability for PCT/EP2010/066462, dated Dec. 12, 2011.

(Continued)

*Primary Examiner* — Kiho Kim
(74) *Attorney, Agent, or Firm* — Nixon & Vanderhye, P.C.

(57) ABSTRACT

The present invention relates to a scanning tool (1) for scanning an object downhole. The tool has a longitudinal axis and comprises an emitting device (2) for emitting radiation, a lens (3) for transmitting the radiation in a predetermined pattern (4) of radiation, and a receiving device (5). In a first position of the tool, the pattern of radiation is reflected on the object (6) to be scanned and the reflected radiation is received in the receiving device resulting in a first measurement.

22 Claims, 8 Drawing Sheets

(56) References Cited

U.S. PATENT DOCUMENTS

| | | | |
|---|---|---|---|
| 5,790,185 A | 8/1998 | Auzerais et al. | |
| 6,355,928 B1* | 3/2002 | Skinner et al. | 250/269.1 |
| 7,350,568 B2* | 4/2008 | Mandal et al. | 166/254.2 |
| 8,374,835 B2* | 2/2013 | Lind et al. | 703/7 |
| 8,636,061 B2* | 1/2014 | Mosse et al. | 166/250.01 |
| 2003/0122094 A1* | 7/2003 | Donlon et al. | 250/584 |
| 2005/0189412 A1* | 9/2005 | Hudnut et al. | 235/383 |
| 2009/0161715 A1* | 6/2009 | Asada et al. | 372/45.01 |

FOREIGN PATENT DOCUMENTS

| | | | |
|---|---|---|---|
| EP | 0 288 134 | 7/1987 | |
| WO | WO 2006088845 A2 * | 8/2006 | G01S 13/89 |

OTHER PUBLICATIONS

First Office Action and English Translation of Text issued in corresponding Chinese Application No. 2010800490250, issued Apr. 1, 2014, 16 pages.

* cited by examiner

SCANNING TOOL

This application is the U.S. national phase of International Application No. PCT/EP2010/066462, filed 29 Oct. 2010, which designated the U.S. and claims priority to Europe Application No. 09174666.9, filed 30 Oct. 2009, the entire contents of each of which are hereby incorporated by reference.

FIELD OF THE INVENTION

The present invention relates to a scanning tool for scanning an object downhole. The tool has a longitudinal axis and comprises an emitting device for emitting radiation, a lens for transmitting the radiation in a predetermined pattern of radiation, and a receiving device.

BACKGROUND ART

A completion comprises several hardware components. The casing string is built as a long line of tubing parts mounted together by means of casing collars and, to optimise production, valves are built in as part of the casing string.

Sometimes, leaks may occur, which must be found and sealed off if they are not to impair the production. For this purpose, a tool capable of identifying the condition of the well and detecting the leak is required.

During production, the valves have to be opened or closed. However, a valve may be covered by scales or the like, sometimes to an extent which makes operation of the valve impossible, or the valve may be so damaged by previous attempts to operate it that it can no longer be opened or closed by conventional tools. In order to determine whether the valve needs cleaning or whether a new key to operate the valve is needed, a tool which is able to identify the condition of the hardware in the well is required.

DESCRIPTION OF THE INVENTION

It is an object of the present invention to provide a downhole tool capable of identifying the condition of the well and the condition of the hardware used in the completion.

It is moreover an object to provide a tool capable of outlining or picturing the hardware and casing wall.

The above objects, together with numerous other objects, advantages, and features, which will become evident from the below description, are accomplished by a solution in accordance with the present invention by a scanning tool for scanning an object downhole, the tool having a longitudinal axis and comprising:
  an emitting device for emitting radiation,
  a lens for transmitting the radiation in a predetermined pattern of radiation, and
  a receiving device,
wherein, in a first position of the tool, the pattern of radiation is reflected on the object to be scanned and the reflected radiation is received in the receiving device resulting in a first measurement.

The above scanning tool makes it possible to scan the inside surface of the well line by line or in another pattern. When subsequently combining the sequence of images, an image can be created showing the object or part of the object in a way which makes it possible for an operator to evaluate the object by a visual inspection of the scanned image and thus determine what to do in order to fix a specific problem. The entire well may be scanned in this way in order to evaluate the condition of the well and to determine which parts of the well needs repair work.

In one embodiment of the invention, a second measurement may be conducted in a second position of the tool.

The scanning tool may further comprise a driving unit for moving at least the lens and the receiving device along the longitudinal axis and conducting a second measurement at a distance from the first measurement and in this way scan the object by emitting the pattern at a distance from the previous emitted pattern, and by repetition thus providing a sequence of measurements. The emitted pattern may be a line.

The driving unit may be a downhole tractor or a conveying unit arranged inside the tool, and it may move at least the lens and the receiving device at least 0.1 mm between the first and the second measurements. In this way, at least the lens and the receiving device have been moved at least 0.1 mm between every two images.

The lens may be a plano-convex cylinder lens.

Moreover, the receiving device may be a recording device and it may be arranged along the longitudinal axis.

In one embodiment of the tool, the emitting device may emit the radiation in a direction transverse to the longitudinal axis.

In addition, the tool may comprise a plurality of emitting devices.

The lens may be torus-shaped.

In one embodiment, the tool may comprise a mirror device for reflecting the pattern reflected on the object before it is received in the receiving device. The mirror may be conical.

When the tool comprises a mirror device, light from the well may thus be reflected in a way which enables the entire circumference around the mirror to be imaged by a single recording device.

Moreover, the lens and the emitting device may be comprised in a line generator.

Furthermore, a measurement may be conducted at a rate of 1 to 200 measurements per second, preferably at a rate of 10 to 50 measurements per second.

In addition, the scanning tool may comprise a positioning tool for determining the position of the scanning tool.

The invention further relates to a system for creating an image of the condition inside a well, comprising:
  a scanning tool according to any of the preceding claims, and
  a calculation unit.

Finally, the invention also relates to a method comprising the steps of:
  inserting a scanning tool according to any of the preceding claims into a well,
  emitting a line of radiation,
  detecting the reflected line,
  moving at least part of the scanning tool in order to illuminate a new part of the well, and
  analysing the reflected line in order to identify the condition of the well.

The method may further comprise the step of creating an image of the analysed reflected line in order to create an image of the well from within.

BRIEF DESCRIPTION OF THE DRAWINGS

The invention and its many advantages will be described in more detail below with reference to the accompanying schematic drawings, which for the purpose of illustration show some non-limiting embodiments and in which.

All the figures are highly schematic and not necessarily to scale, and they show only those parts which are necessary in order to elucidate the invention, other parts being omitted or merely suggested.

DETAILED DESCRIPTION OF THE INVENTION

Figure 1A:
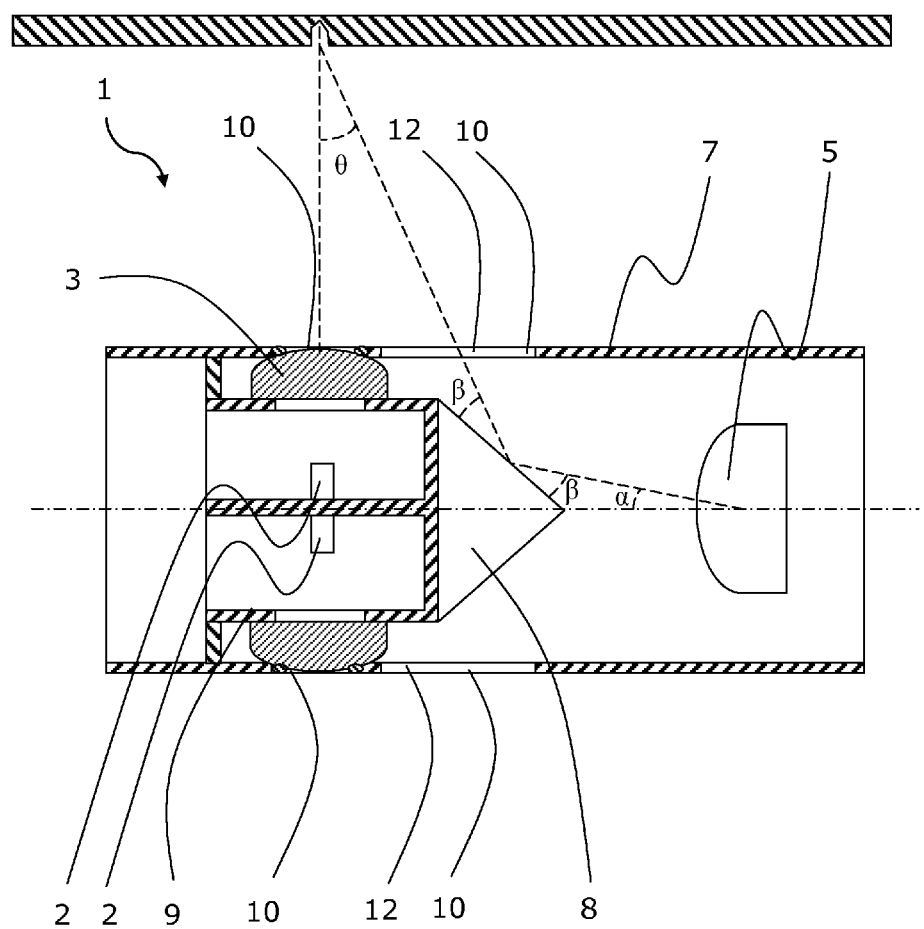
FIG. 1A shows a partly cross-sectional view of a scanning tool according to the invention seen from a side.
Figure 1B:
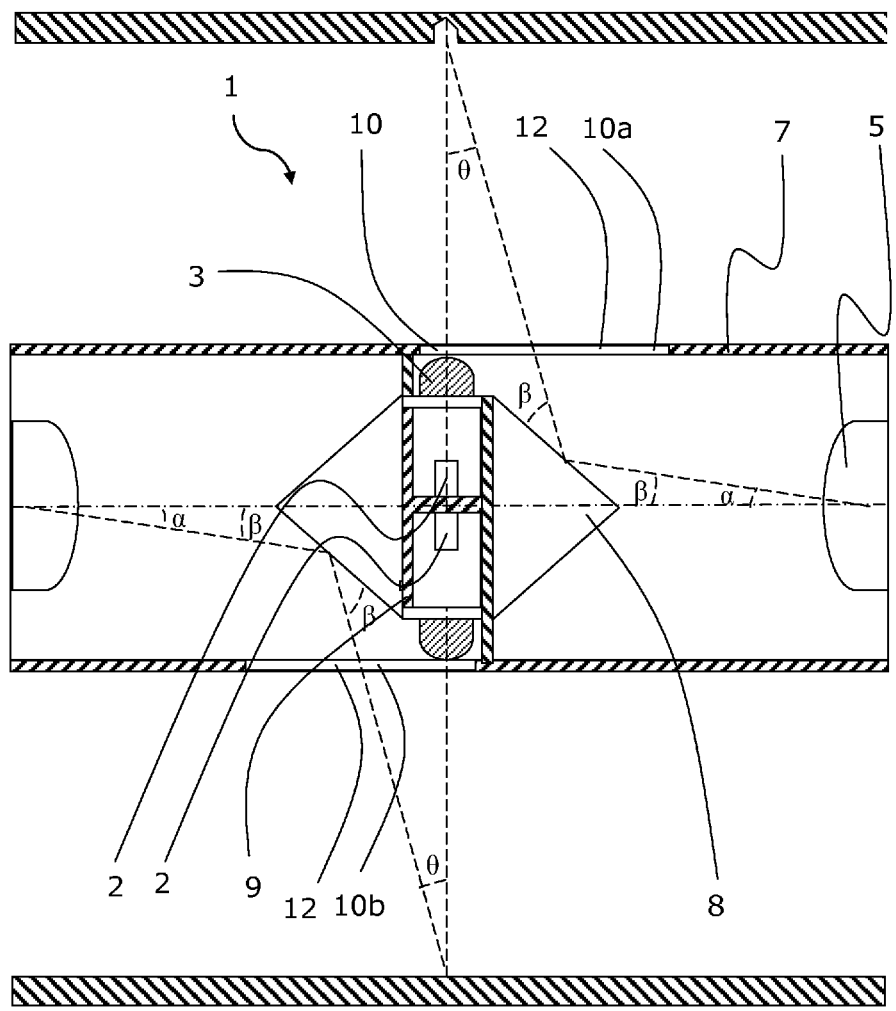
FIG. 1B shows a partly cross-sectional view of another embodiment of the scanning tool according to the invention seen from a side.
Figure 5:
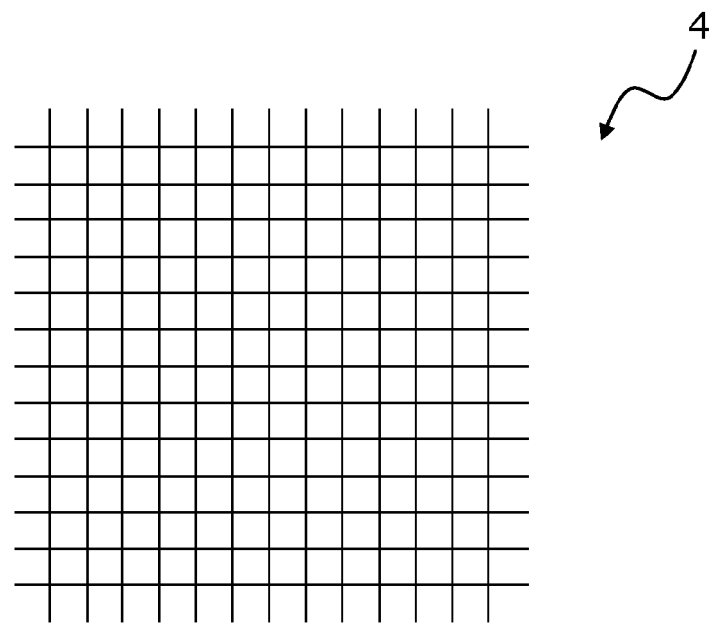
FIG. 5 shows a grid.
Figure 6:
FIG. 6 shows a line.

In FIG. 1A, part of a scanning tool 1 according to invention is shown. The scanning tool 1 is capable of scanning an object downhole, e.g. line by line, when the tool or part of the tool is moved in relation to the object to be scanned. The scanning tool 1 comprises an emitting device 2 for emitting radiation into a lens 3. The lens 3 transmits the radiation in a predetermined pattern 4 of radiation, such as a line as shown in FIGS. 1A, 1B, and 6, a grid as shown in FIG. 5, or another suitable pattern. The pattern 4 is reflected on the inside wall of the casing or borehole and is subsequently detected by a receiving device 5.

In the following, the invention is explained on the basis of an object present in the well, such as a valve arranged as part of the casing wall, perforations in the casing, a sleeve, a packer, or the like hardware elements in a well. Thus, the scanning tool 1 may be used to detect whether a sliding sleeve is open, partly closed, or closed. Subsequently, another operation tool can be submerged in order to close or open the sleeve, or clean the object. When the other operation tool has finished its operation, the scanning tool 1 can be submerged once more to inspect the object again.

In this way, the pattern 4 of radiation is reflected on an object to be scanned and the reflected radiation is received in the receiving device 5, which is a camera, an image sensor, or the like processor. The receiving device 5 may have a lens provided in front of the camera seen in relation to the emitting device 2.

Figure 4:
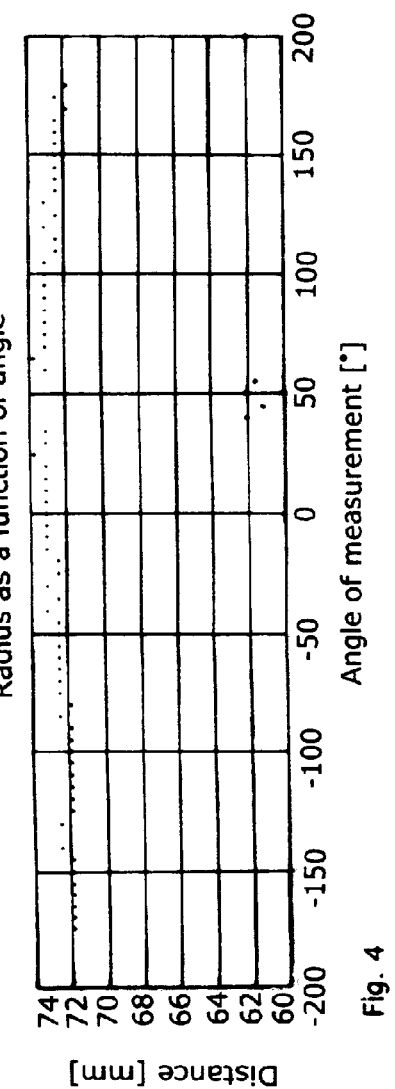
FIG. 4 shows a second graph of the measurements of FIG. 3 in polar coordinates.

The scanning tool 1 comprises an elongated housing 7 with a plurality of slots or openings 10 allowing radiation in the form of light to be emitted from the tool and enter the tool again. Inside the housing 7, the torus-shaped lens 3 is illuminated from within by the emitting device 2. In order to illuminate the whole lens 3, several emitting devices 2 are arranged inside the torus. In FIG. 1A, twenty emitting devices 2 are arranged inside the lens 3. The lens 3 guides the radiation into a pattern 4, such as a line, and irradiates the object to be scanned with that pattern. The pattern 4 is reflected by the surface of the object to be scanned and returned at an angle θ so as to be reflected by a mirror 8 before being received in the receiving device 5. The mirror 8 is cone-shaped and, in this embodiment, the pattern 4 is a line which is reflected as a circle by the mirror, as illustrated in FIG. 4. The mirror 8 is mounted onto the housing 7 by means of a mounting device 9 onto which the emitting device 2 is also fastened. The mounting device 9 is provided with a circumferential slot allowing the radiation of the emitting devices 2 to illuminate the lens 3. Having a mirror 8 makes it possible to arrange the receiving device 5 axially displaced in relation to the lens 3.

Thus, the lens 3 has a radial extension transverse to the longitudinal extension of the tool 1. The emitting devices 2 are arranged so that they irradiate the lens 3 in a radial direction. The mirror 8 is arranged on one side of the lens 3 at an axial distance from the lens 3 in relation to the axis of the tool 1 and tapers away from the emitting devices 2 and the lens. The receiving device 5 is arranged at an axial distance from the mirror 8 even further away from the lens 3.

In another embodiment, only three emitting devices 2 are arranged inside the lens 3. Such emitting devices 2 must have a wider emitting range in order to illuminate the whole lens 3.

Sealing means 11 in the form of an O-ring is arranged between the lens 3 and the housing 7 in order to seal off the inside of the tool 1. Furthermore, the slot 10 through which the reflected radiation enters the housing again may be provided with a window 12 also sealing off the inside of the housing, but also letting the light through.

In another embodiment, the surrounding part of tool 1 is a glass housing which surrounds a frame part of the tool, which in this case is also the mounting device 9 of the tool.

In FIGS. 1A and 1B, the lens 3 generates a radiation pattern 4 in the form of a line and is a plano-convex cylinder lens. However, the lens 3 may be any suitable lens capable of generating a pattern, such as a line, a grid, etc.

Another embodiment of the tool 1 is shown in FIG. 1B, in which embodiment the tool has two mirrors 8 and two receiving devices 5 positioned opposite each other so that a mirror and a receiving device is positioned on each side of the lens 3. In this embodiment, the mounting device 9 has a frame configuration providing a strong tool design. The frame has openings 10 displaced in relation to one another so that a first opening 10a is displaced in relation to a second opening 10b. Each opening 10 is adapted to both emit radiation and let in reflected radiation to be reflected by the mirror 8 and transmitted into the receiving device 5. Each of the receiving devices 5 receives only part of the reflected radiation so that one part of the pattern is received in one receiving device 5 and another part is received in the other receiving device 5. When these parts of the reflected pattern are joined, the whole pattern can subsequently be processed as explained below.

The entire mounting device 9 may be surrounded by only one glass housing providing a simple encapsulation of the mounting device and a design which seals off the tool 1 towards the outside well fluid in a simple manner.

The receiving device 5 of FIGS. 1A and 1B receives the reflected line as a circle or parts of a circle due to the conical shape of the mirror 8. The receiving device receives light from a small part of the casing and each point on the object, e.g. the inside of the casing, is mapped to a point between two concentric circles in the two-dimensional image plane. Thus, the radiated line in the image corresponds to a plurality of points on the casing.

In this embodiment, the pattern 4 is a line emitted as a circle all the way around the tool 1 towards the inside of the casing to scan the casing. The pattern 4 may be any kind of pattern emitted as a closed contour on an object to be scanned, in the illustrated example as a circle which is received in the tool 1 again as a circle if the inside of the casing wall is smooth, or as parts of concentric circles if the casing wall has a projection or an indentation.

Figure 3:
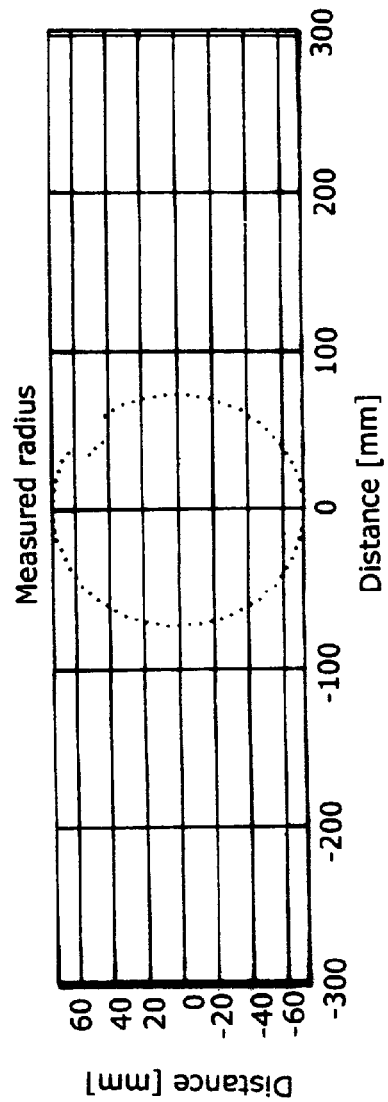
FIG. 3 shows a graph of measurements, based on the image of FIG. 7, in Cartesian coordinates.
Figure 7:
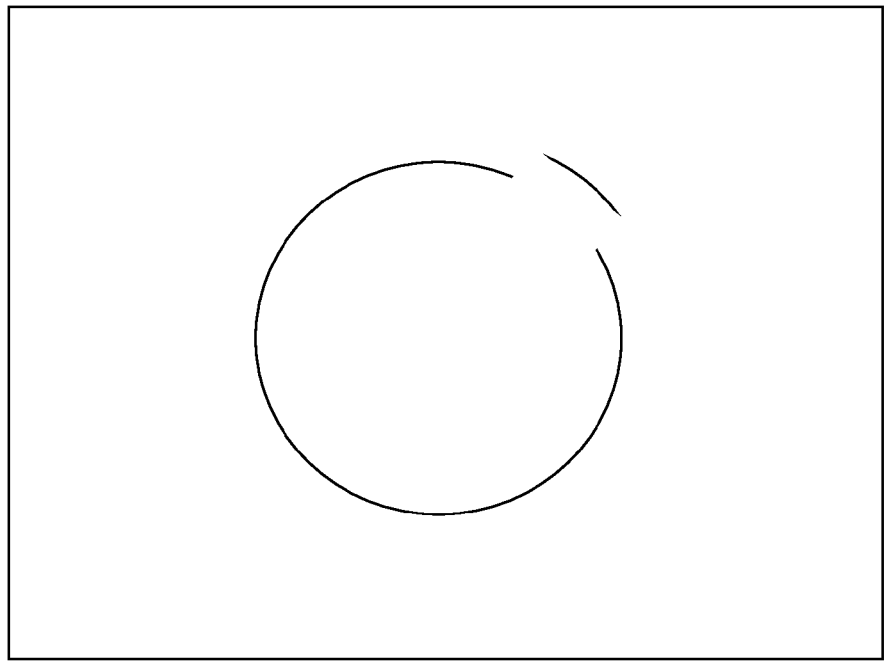
FIG. 7 shows the recorded image that, after transformation, resulted in the measurements shown in FIGS. 3 and 4.

Moreover, an image sensor connected with the receiving device 5 converts the image of a circle or parts of concentric circles, as shown in FIG. 7, into data, as shown in FIG. 3. In FIG. 7, the circle has been broken and a piece of the circle has been displaced. The reason for this is that the emitted line has been reflected on an object having an indentation corresponding to the piece of the line that has been displaced. The data in FIG. 3 show the same displacement. The data in FIG. 3 is viewed in a different way in FIG. 4, also illustrating the emitted line. At the angle 50, four data points have been displaced in the same way. If the object had had several indentations, a corresponding number of points would have been displaced. If the object had had a projection instead of an indentation, the piece of line would have been displaced in the opposite direction, i.e. outwards and away from the centre, in FIG. 4.

Figure 7A:
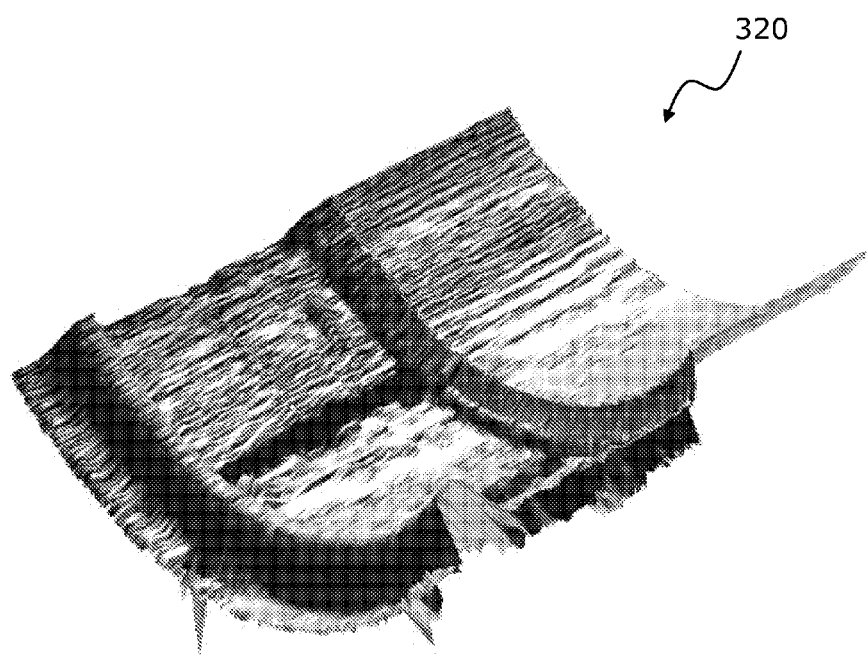
FIG. 7A shows a sequence of recorded images of a sleeve combined to create an image of the sleeve.

When the images of FIG. 7 are combined in sequence, an image 320 of the object to be scanned is created as a scanned image 320 of either the whole section of the object or the inside of the well as shown in FIG. 7A. FIG. 7A shows an image of a sleeve scanned line by line by the scanning tool created by combining the sequence of reflected lines. Having such a scanned image 320 of a whole section of the sleeve makes it possible to determine whether the sleeve is open, partly opened, or closed, and whether scales fasten to the sleeve hinder the operation of the sleeve.

By scanning an object line by line or in another pattern, an image can be created picturing the object or part of the object in a way which makes it possible for an operator to evaluate the object by visually inspecting the scanned image and thus to determine what to do in order to fix a certain problem. The entire well may be scanned in this way in order to evaluate the condition of the well and to determine which parts of the well needs repair work, if any.

The distance between the displaced piece and the rest of the circle indicates the depth of the indentation or the height of the projection. Similarly, the length of the displaced line piece in relation to the length of the circumference of the rest of the circle indicates the circumferential length of the indentation in the object to be scanned. Thus, an exact image of the whole object can be calculated from the data retrieved when scanning the object.

Figure 2:
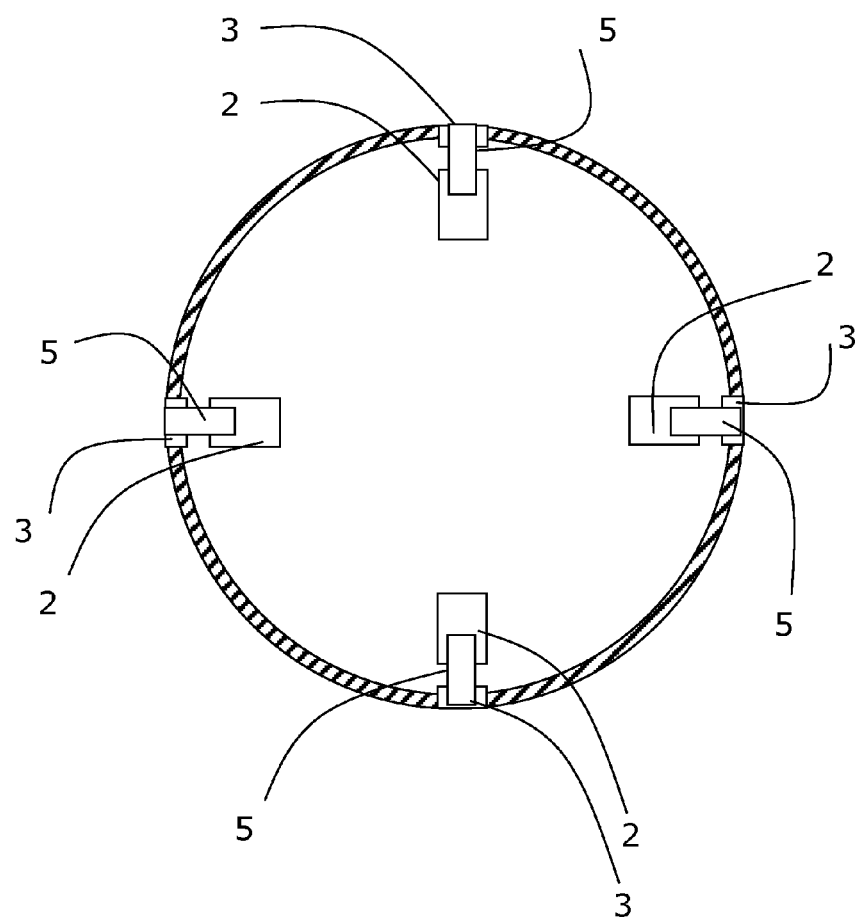
FIG. 2 shows a partly cross-sectional view of another embodiment of the scanning tool seen from one end.

In FIG. 2, the scanning tool 1 comprises four lenses 3 arranged spaced apart along the periphery of the tool housing 7. Each lens 3 is illuminated by an emitting device 2 situated radially behind the lens in a direction towards the centre of the tool 1. Each lens 3 is capable of transmitting a line radially, the lines of the four lenses thus overlapping each other and together defining one circumferential line. Next to each lens 3 in the axial extension of the tool, a receiving device 5 is arranged for receiving the line when reflected by the object. In the embodiment of FIG. 2, no mirror is needed in order to scan the object, since the each receiving device 5 is arranged next to a lens 3 receiving the reflected radiation radially.

In some cases, more lenses 3, emitting devices 2, and receiving devices 5 may be needed in order to scan an object depending on the object itself, the distance to the object, and the fluid in the well. The more transparent the well fluid, the less illumination is needed for scanning the object properly.

In another embodiment, only one lens 3, emitting device 2, and receiving device 5 are arranged in the tool 1. The tool 1 is then at least partly rotated to scan the inside of the well. The tool 1 thus comprises rotation means for rotating part of the tool or the whole tool. In this case, the pattern 4 may be a single point rotated into creating a line on the inside of the casing wall.

The lens 3 and the emitting device 2 may be arranged in the tool 1 as one unit, e.g. comprised in a line generator. Furthermore, the tool 1 may comprise several lenses 3 for each emitting device 3, resulting in the creation of a grid as shown in FIG. 6, or the lens may be covered in order to create the grid pattern. In another embodiment, the emitting device comprises a grid generator.

Figure 8:
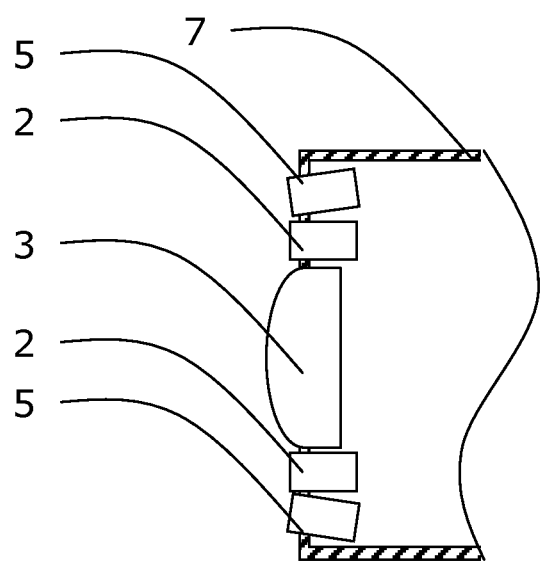
FIG. 8 shows a partly cross-sectional view of yet another embodiment of the tool.

As shown in FIG. 8, the pattern 4 may be emitted in front of the tool 1 by several emitting devices 2 to obtain information concerning objects in front of the tool, such as valve, or objects positioned as part of the casing wall, but narrowing the casing, such as a "no-go landing nipple" or the like. As can be seen, the cameras are angled towards the centre axis of the tool 1 and they are thus able to detect the same pattern 4 from different angles, creating a three-dimensional image of the object. In another embodiment, the pattern 4 may be created by a grid generator arranged behind the lens 3 in FIG. 8 instead of by emitting devices 2 arranged around the lens in front of the tool 1.

The scanning tool 1 may be used as a positioning tool, since it is capable of detecting a casing joint, a sleeve, or another object. Based on the information on the design of the object, the images can be put together to match the dimensions of the known object and, based on information on the frequency with which the images are taken, it is possible to estimate the velocity of the scanning tool 1.

The scanning tool may also comprise a positioning tool in order to determine the position of each image. If a leak is detected, an operation tool may thus subsequently be submerged at the exact position in order to seal off the leak.

The images may be received and at least partly processed by the receiving device at a rate of 10-200 images per second, preferably 20-100 images per second, and even more preferably 20-50 images per second. When an image is received, it is converted into data, such as electronic signals. This data is compared to the data of the image previously taken and only the differences between the data are communicated to the top of the well or above surface to reduce the total amount of data. When the amount of data is thus reduced, an image can quickly be created on a PC screen, making it possible for the operator to follow the investigation as it is performed.

The data may also be compressed in conventional ways before being sent to the top of the well or above surface. It may also be downloaded into a buffer, such as a data memory. If no change is detected, the scanning tool 1 may then transmit a signal to the top of the well that there is no change.

The mirror 8 may have any suitable shape, such as a pyramid shape, a semi-sphere, or the like.

The emitting device 2 emits electromagnetic radiation with a frequency of $10^{11}$-$10^{19}$ Hz, such as X-rays, UV, visible light, and infrared light. The emitting device 2 may thus be a laser or another radiation device.

When the well fluid which the radiation of the scanning tool 1 has to penetrate is water or gas, light having a frequency of 750 nm is sufficient. However, when the fluid is mostly oil, the emitted radiation could be another type of radiation, such as radiation closer to the infrared area or closer to UV.

The receiving device 5 may be a camera or an image sensor converting an optical image/pattern to an electric signal.

The tool 1 may also comprise a driving unit for moving at least the lens and the receiving device along the longitudinal axis of the tool for conducting a second measurement at a distance from the first measurement. The object is thus scanned by emitting subsequent patterns at a distance from the previous emitted pattern, providing a sequence of measurements by repetition.

The driving unit may be a conveying unit arranged inside the tool 1, so that only the lens 3 and the receiving device 5 are moved in relation to the tool along its longitudinal axis.

By fluid or well fluid is meant any kind of fluid that may be present in oil or gas wells downhole, such as natural gas, oil, oil mud, crude oil, water, etc. By gas is meant any kind of gas composition present in a well, completion, or open hole, and by oil is meant any kind of oil composition, such as crude oil, an oil-containing fluid, etc. Gas, oil, and water fluids may thus all comprise other elements or substances than gas, oil, and/or water, respectively.

By a casing is meant any kind of pipe, tubing, tubular, liner, string etc. used downhole in relation to oil or natural gas production.

In the event that the tools are not submergible all the way into the casing, a downhole tractor can be used to push the tools all the way into position in the well. A downhole tractor is any kind of driving tool capable of pushing or pulling tools in a well downhole, such as a Well Tractor®.

Although the invention has been described in the above in connection with preferred embodiments of the invention, it will be evident for a person skilled in the art that several modifications are conceivable without departing from the invention as defined by the following claims.

The invention claimed is:

1. A scanning tool configured to scan an object downhole located in a fluid environment containing natural gas, oil, oil mud, crude oil, or water, the scanning tool comprising:
   a tool body having a longitudinal axis, the tool body comprising:
      an emitting device configured to emit electromagnetic radiation in the form of ultraviolet light (UV), visible light or infrared light,
      a lens configured to transmit the electromagnetic radiation in a predetermined pattern of radiation,
      a receiving device configured to receive the electromagnetic radiation, and
      a mirror device configured to reflect the pattern reflected by the object before it is received in the receiving device;
   wherein, in a first position of the tool, the pattern of radiation is reflected on a surface of the object to be scanned and the reflected electromagnetic radiation is received in the receiving device resulting in a first measurement.

2. A scanning tool according to claim 1, wherein a second measurement is conducted in a second position of the tool.

3. A scanning tool according to claim 1, further comprising a driving unit for moving at least the lens and the receiving device along the longitudinal axis and conducting a second measurement at a distance from the first measurement and in this way scan the object by emitting the pattern at a distance from the previous emitted pattern, and by repetition thus providing a sequence of measurements.

4. A scanning tool according to claim 3, wherein the driving unit is a conveying unit arranged inside the tool.

5. A scanning tool according to claim 3, wherein the driving unit moves at least the lens and the receiving device at least 0.1 mm between the first and the second measurements.

6. A scanning tool according to claim 1, wherein the pattern is a line.

7. A scanning tool according to claim 1, wherein the lens is a plano-convex cylinder lens.

8. A scanning tool according to claim 1, wherein the receiving device is a recording device.

9. A scanning tool according to claim 1, wherein the emitting device emits the electromagnetic radiation in a direction transverse to the longitudinal axis.

10. A scanning tool according to claim 1, wherein the mirror is conical.

11. A system for creating an image of the condition inside a well, comprising
   a scanning tool according to claim 1, and
   a calculation unit.

12. A method comprising the steps of:
   inserting a scanning tool according to claim 1 into a well,
   emitting a line of electromagnetic radiation with a frequency of $10^{11}$-$10^{19}$ Hz,
   detecting the reflected line,
   moving at least part of the scanning tool in order to illuminate a new part of the well,
   analysing the reflected line, and
   creating an image of the analysed reflected line in order to create an image of the well from within and to identify the condition of the well.

13. A scanning tool according to claim 1, wherein the emitting device is a laser.

14. A scanning tool according to claim 1, wherein a measurement is conducted at a rate of 5-100 measurements per second.

15. A scanning tool according to claim 1, wherein a measurement is conducted at a rate of 10-50 measurements per second.

16. A scanning tool according to claim 1, wherein the object is a valve and the surface is a surface of the valve.

17. A scanning tool according to claim 1, wherein the object is a casing and the surface is an inside surface of the casing.

18. A scanning tool configured to scan an object downhole located in a fluid environment containing natural gas, oil, oil mud, crude oil, or water, the scanning tool comprising:
   a tool body having a longitudinal axis, the tool body comprising:
      an emitting device configured to emit electromagnetic radiation in the form of ultraviolet light (UV), visible light or infrared light,
      a lens configured to transmit the electromagnetic radiation in a predetermined pattern of radiation, and
      a receiving device configured to receive the electromagnetic radiation,
   wherein, in a first position of the tool, the pattern of radiation is reflected on a surface of the object to be scanned and the reflected electromagnetic radiation is received in the receiving device resulting in a first measurement; and
   a measurement is conducted at a rate of 1 to 200 measurements per second.

19. A scanning tool according to claim 18, wherein a second measurement is conducted in a second position of the tool.

20. A scanning tool according to claim 18, further comprising a driving unit for moving at least the lens and the receiving device along the longitudinal axis and conducting a second measurement at a distance from the first measurement and in this way scan the object by emitting the pattern at a distance from the previous emitted pattern, and by repetition thus providing a sequence of measurements.

21. A scanning tool according to claim 18, wherein the emitting device emits the electromagnetic radiation in a direction transverse to the longitudinal axis.

22. A scanning tool according to claim 18, wherein the emitting device is a laser.

* * * * *